(12) United States Patent
Katsumata et al.

(10) Patent No.: US 10,675,275 B2
(45) Date of Patent: Jun. 9, 2020

(54) PROPHYLACTIC AND/OR THERAPEUTIC AGENT FOR FIBROMYALGIA

(71) Applicant: ONO PHARMACEUTICAL CO., LTD., Osaka (JP)

(72) Inventors: Seishi Katsumata, Osaka (JP); Katsukuni Mitsui, Osaka (JP); Yuya Ezaki, Ibaraki (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/542,167

(22) PCT Filed: Jan. 8, 2016

(86) PCT No.: PCT/JP2016/050527
§ 371 (c)(1),
(2) Date: Jul. 7, 2017

(87) PCT Pub. No.: WO2016/111357
PCT Pub. Date: Jul. 14, 2016

(65) Prior Publication Data
US 2018/0169077 A1 Jun. 21, 2018

(30) Foreign Application Priority Data
Jan. 9, 2015 (JP) .................. 2015-002725

(51) Int. Cl.
| A61K 31/438 | (2006.01) |
| A61K 31/405 | (2006.01) |
| A61K 31/5513 | (2006.01) |
| A61K 31/616 | (2006.01) |
| A61K 31/381 | (2006.01) |
| A61K 31/135 | (2006.01) |
| A61K 31/195 | (2006.01) |
| A61K 31/167 | (2006.01) |
| A61K 31/165 | (2006.01) |
| A61K 31/415 | (2006.01) |
| A61K 31/192 | (2006.01) |
| A61K 31/407 | (2006.01) |
| A61P 29/00 | (2006.01) |
| A61K 45/06 | (2006.01) |

(52) U.S. Cl.
CPC .......... *A61K 31/438* (2013.01); *A61K 31/135* (2013.01); *A61K 31/165* (2013.01); *A61K 31/167* (2013.01); *A61K 31/192* (2013.01); *A61K 31/195* (2013.01); *A61K 31/381* (2013.01); *A61K 31/405* (2013.01); *A61K 31/407* (2013.01); *A61K 31/415* (2013.01); *A61K 31/5513* (2013.01); *A61K 31/616* (2013.01); *A61K 45/06* (2013.01); *A61P 29/00* (2018.01)

(58) Field of Classification Search
USPC ........................................................ 514/161
See application file for complete search history.

(56) References Cited

U.S. PATENT DOCUMENTS

2002/0018809 A1 2/2002 Stoll
2008/0114012 A1 5/2008 Ohmoto et al.

FOREIGN PATENT DOCUMENTS

| JP | 2002-541097 A | 12/2002 |
| JP | 2008-260728 A | 10/2008 |
| JP | 4997976 B2 | 8/2012 |
| WO | 2006/068164 A1 | 6/2006 |
| WO | 2009/025091 A1 | 2/2009 |
| WO | 2015/190568 A1 | 12/2015 |

OTHER PUBLICATIONS

Lee (Tramadol 37.5-mg/Acetaminophen 325-mg Combination Tablets Added to Regular Therapy for Rheumatoid Arthritis Pain: A 1-Week, Randomized, Double-Blind, Placebo-Controlled Trial, 2006, Clinical Therapeutics, vol. 28, No. 12, pp. 2052-2060).*
Harris (Newer treatments for fibromyalgis syndrome, Therapeutics and Clinical Risk Management, 2008:4(6), pp. 1331-1342).*
Admin (6 Best Fibromyalgia Pain Killer, 2104, https://www.redorbit.conn/6-fibromyalgia-pain-killers/).*
L. Bazzichi et al; "Peripheral benzodiazepine receptors on platelets of fibromyalgic patients"; Clinical Biochemistry; vol. 39; No. 9; 2006; pp. 867-872; 6 pgs. total.
P. Faggioli et al; "Increase in peripheral benzodiazepine receptors on monocytes in fibromyalgia"; Rheumatology; vol. 43; No. 10; 2004; pp. 1224-1225; 2 pgs. total.
K. Toda et al; "Sen'i Kintsusho"; The Japanese Journal of Psychiatry; vol. 11; No. 1; 2006; pp. 65-73; 19 pgs. total.
T. Miyamae et al; "Wagakuni ni Okeru Sen'i Kintsusho no Jittai to Rinshozo"; The Journal of the Japan Pediatric Society; vol. 112; No. 12; 2008; pp. 1769-1777; 18 pgs. total.
K. Nishioka; "Totsu Model kara Itami o Miru 2 Sen'i Kintsusho Model"; Biomedicine & Therapeutics; vol. 39; No. 8; 2005; pp. 806-809; 9 pgs. total.
H. Kiyama; "CNS-mediated disintegration of homeostasis by chronic stress"; Folia Pharmacologica Japonica; vol. 142; No. 5; 2013; pp. 210-214; 9 pgs. total.
K. Ota; "Sen'i Kintsusho ni Gappei suru Restless Legs Shokogun ni Taisuru Pramipexole, Gabapentin enacarbil Heiyo Chiryo no Koka"; Pain Clinic; vol. 34; No. 12; 2013; pp. 1671-1677; 16 pgs. total.
C. Braestrup, et al; "Specific bensodiazepine receptors in rat brain characterized by high-affinity [³H] diazepam binding"; Proc. Natl. Acad. Sci. USA; vol. 74; No. 9; Sep. 1977; pp. 3805-3809; 5 pgs. total.
International Search Report dated Mar. 15, 2016 issued by the International Searching Authority in counterpart International Application PCT/JP2016/050527 (PCT/ISA/210).
Written Opinion dated Mar. 15, 2016 issued by the International Searching Authority in counterpart International Application PCT/JP2016/050527 (PCT/ISA/237).
Mitsui Katsukuni et al; "Effects of Ono-2952, a Novel Translocator Protein 18kda Antagonist, on Stress-Induced Rectal Hyperalgesia and Defecation in Rats"; Gastroenterology; vol. 142; No. 5 Suppl. 1; Jan. 1, 2012; pp. S813-S814; 2 pgs. Total XP009500677.
Communication dated Nov. 7, 2017 issued by the European Patent Office in counterpart European application No. 16735096.6.

* cited by examiner

*Primary Examiner* — Kathrien A Cruz
(74) *Attorney, Agent, or Firm* — Sughrue Mion, PLLC

(57) ABSTRACT

(1S)-2-acetyl-1-(4-chloro-2-methoxyphenyl)-5-fluoro-1,2,3,9-tetrahydrospiro[β-carboline-4,1'-cyclopropane] can significantly suppress a decrease of a pain threshold compared to well-known TSPO antagonists, and thus can be an excellent prophylactic and/or therapeutic agent for fibromyalgia, fibromyalgia-associated diseases, and fibromyalgia-associated symptoms.

3 Claims, 4 Drawing Sheets

[Fig. 1]
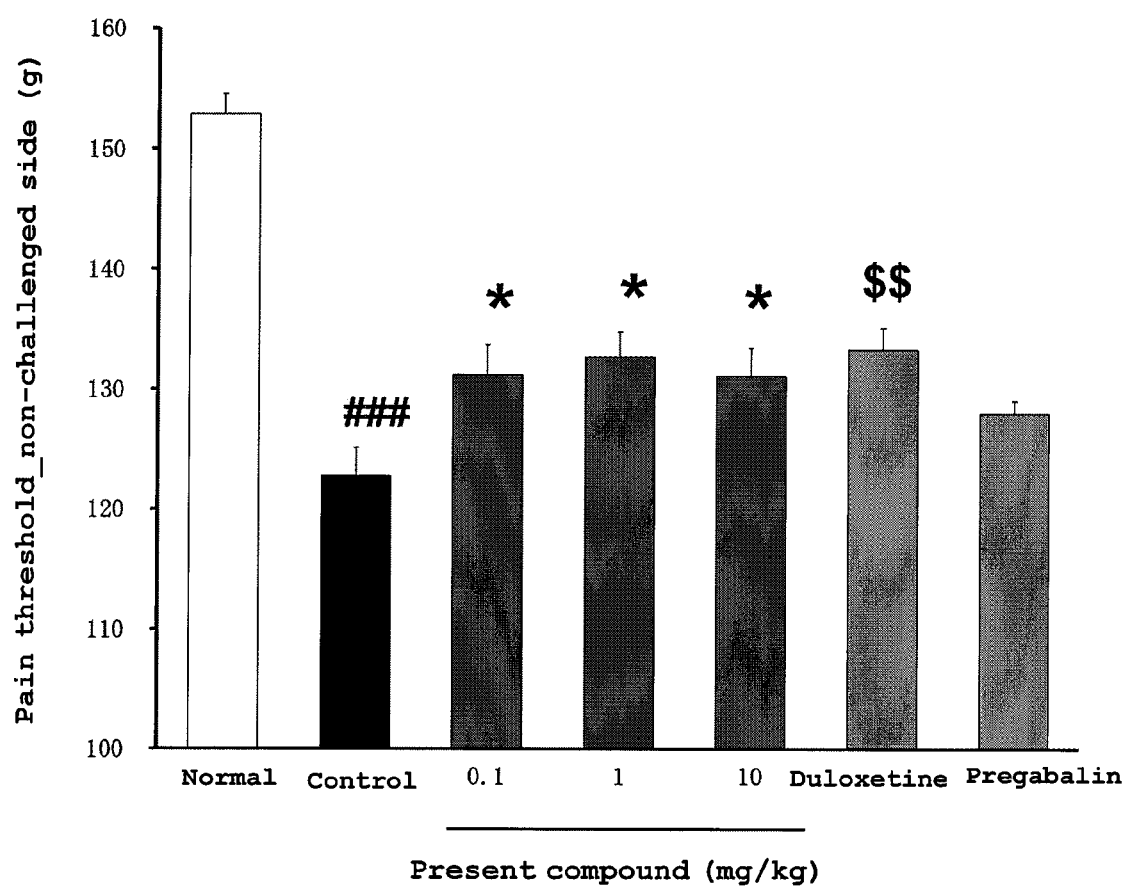

[Fig. 2]
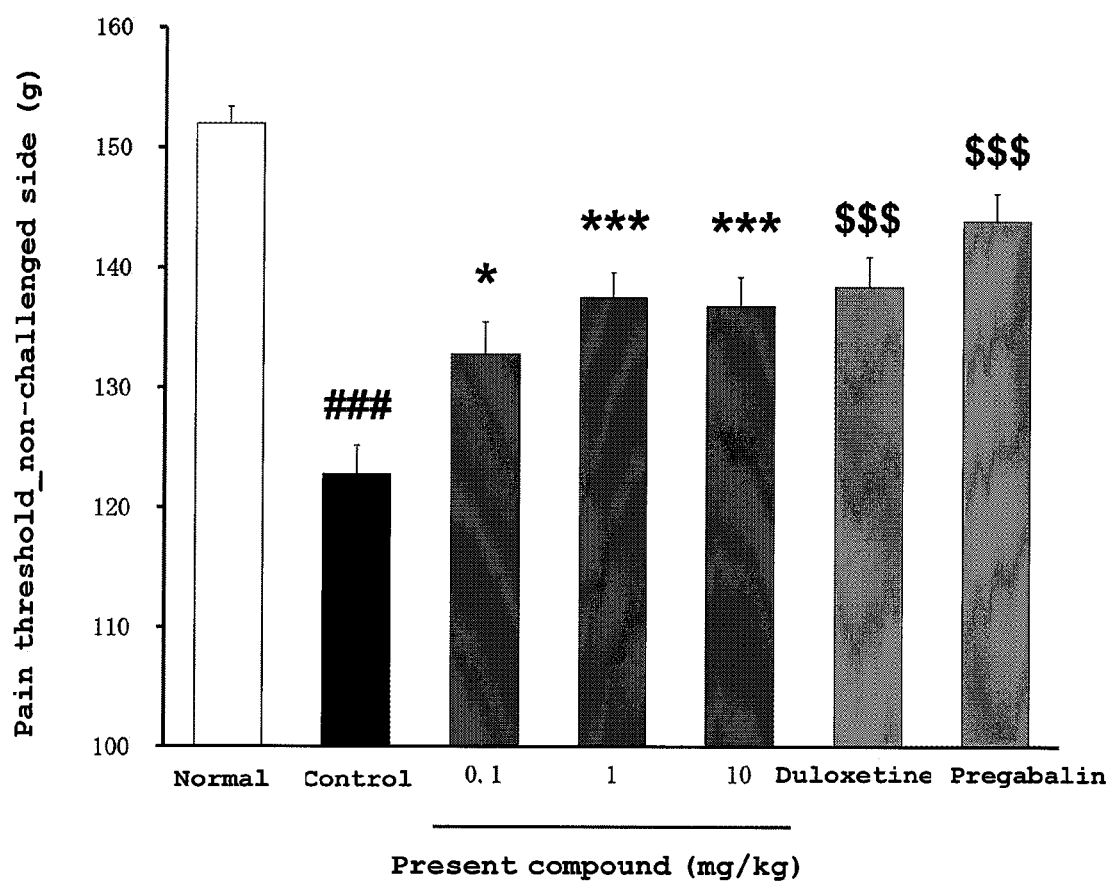

[Fig. 3]
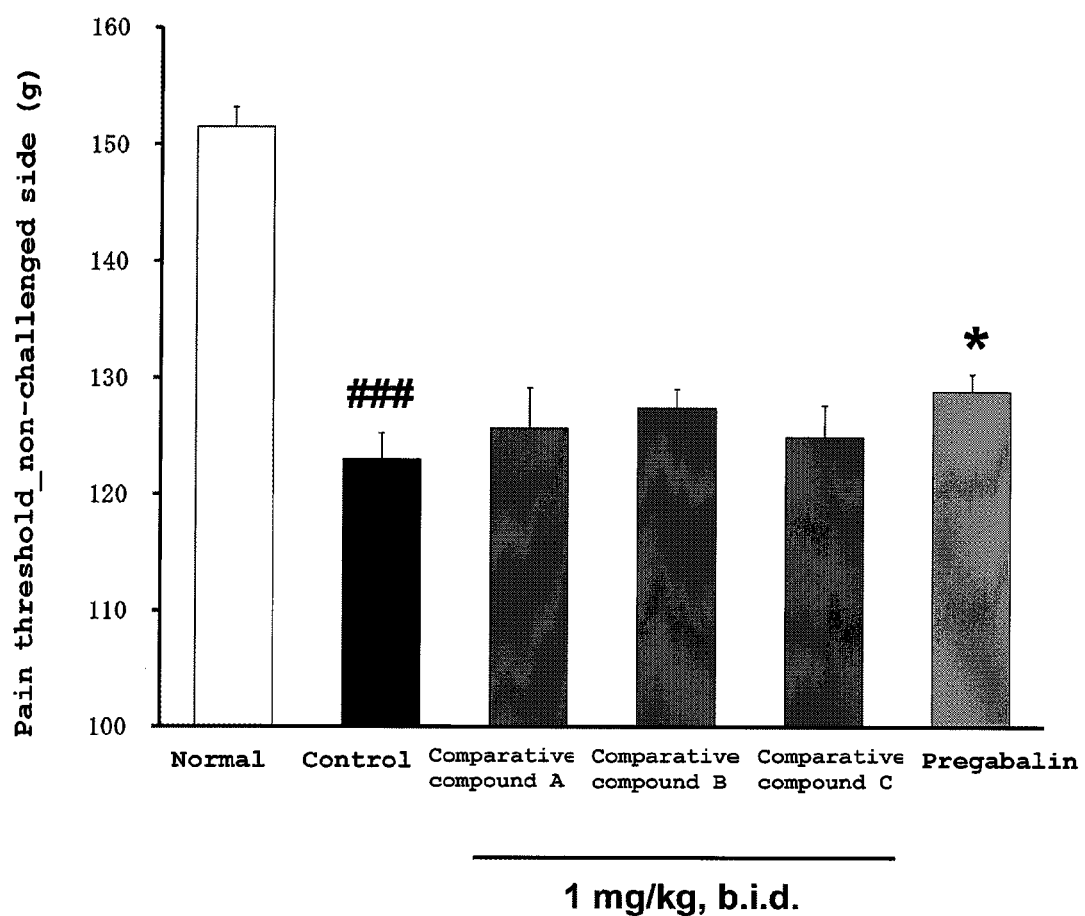

[Fig 4]
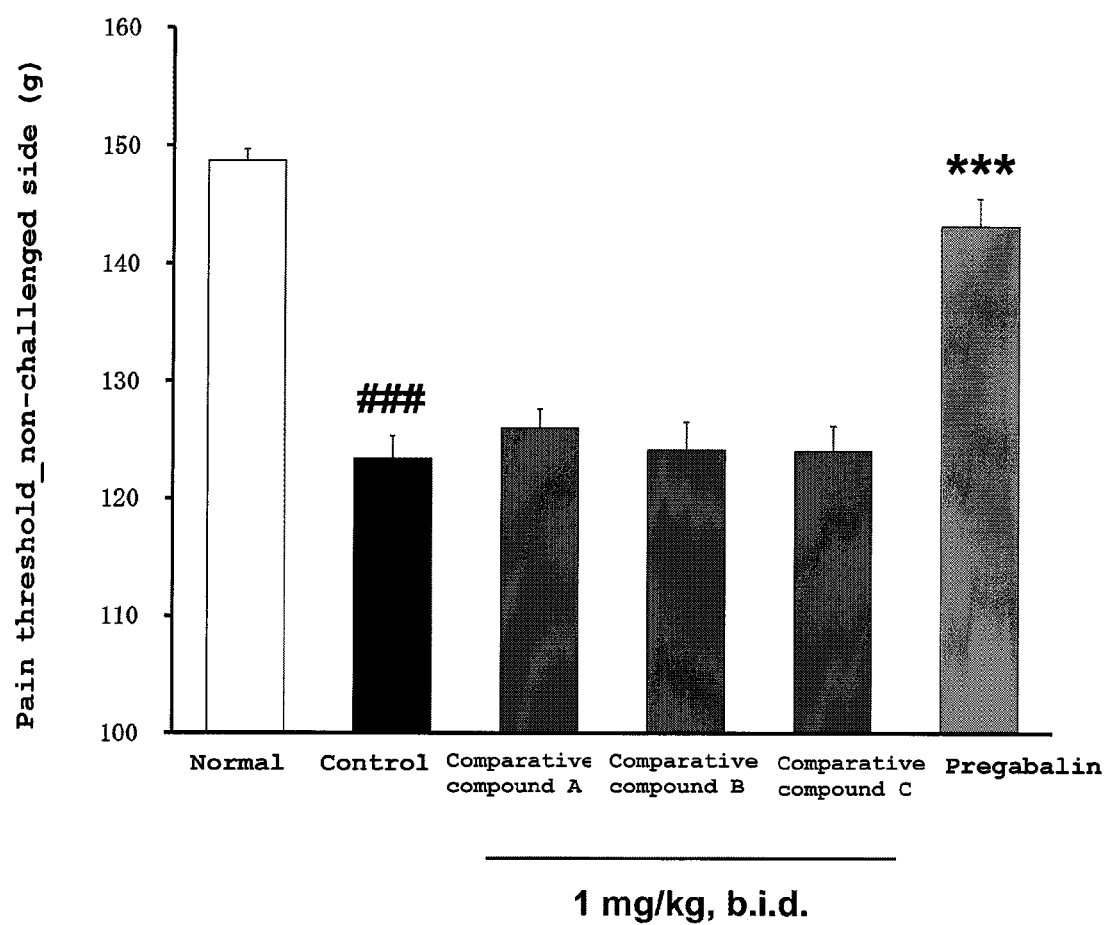

PROPHYLACTIC AND/OR THERAPEUTIC AGENT FOR FIBROMYALGIA

CROSS-REFERENCE TO RELATED APPLICATIONS

This application is a 371 national stage of International Application No. PCT/JP2016/050527 filed Jan. 8, 2016, and claims priority from JP Application No. 2015-002725 filed Jan. 9, 2015, the entires disclosures of which are incorporated by reference herein.

TECHNICAL FIELD

The present invention relates to a prophylactic and/or therapeutic agent for fibromyalgia, characterised in that (1S)-2-acetyl-1-(4-chloro-2-methoxyphenyl)-5-fluoro-1,2,3,9-tetrahydrospiro[β-carboline-4,1'-cyclopropane] (hereinafter also abbreviated as "the present compound") is administered.

BACKGROUND ART

Fibromyalgia (FM) is a disease of which the main symptom is systemic pain persistent for 3 months or more and it is known that the disease is triggered by chronic stress, psychological trauma, acute diseases and the like. Because the main symptom, pain, diffuses to entheses, muscles and joints and from extremities to the whole body and continues over a long period of time, the quality of life (QOL) of patients is significantly decreased. The prevalence of the disease is about 2% in Japan, Germany and the United States of America according to epidemiological researches and currently about 2 million people are suffering from the disease in Japan. The marketed drugs that may treat pains accompanied with fibromyalgia so far include pregabalin, duloxetine, milnacipran and the like. However, as the drugs alleviate pain and thus only palliative therapy is available, there is a need for a drug that can radically cure fibromyalgia.

Meanwhile, TSPO (translocator protein 18 kDa) is a protein also referred to as MBR (mitochondrial benzodiazepine receptor) or PBR (peripheral benzodiazepine receptor) and attracts attention as a pharmacological target of stress diseases typically including irritable bowel syndrome (IBS). It is known that TSPO exists at the mitochondrial outer membrane of various cells such as macrophages, microglia and reactive astrocytes and involved in cholesterol transportation and steroid production (see NPL 1). It is believed that under stressed conditions, the amount of neurosteroids, a type of steroids, in the brain changes, the balance between the excitatory and inhibitory signal transduction systems is disrupted, thereby changing the activities in the nervous system, the immune system and the endocrine system and causing various stress diseases. It has been recently reported that expression of TSPO is elevated in monocytes of fibromyalgia patients (see NPL 2) and that expression of TSPO is also elevated in thrombocytes of fibromyalgia patients (see NPL 3).

However, the prior art documents merely disclose an elevated expression of TSPO observed in fibromyalgia patients and do not disclose or suggest that the present compound which has an antagonistic effect of TSPO (see PTL 1) can be an excellent therapeutic agent for fibromyalgia compared to well-known TSPO antagonists.

CITATION LIST

Patent Literature

[PTL 1] WO 2006/068164

Non Patent Literature

[NPL 1] Proceedings of the National Academy of Science of the United States of America, vol. 89, pp. 3805-3809, 1977
[NPL 2] Rheumatology, vol. 43, pp. 1224-1225, 2004
[NPL 3] Clinical Biochemistry, vol. 39, pp. 867-872, 2006

SUMMARY OF INVENTION

Technical Problem

An object of the present invention is to provide an excellent prophylactic and/or therapeutic agent for fibromyalgia.

Solution to Problem

The inventors of the present invention carried out extensive studies in order to solve the problem and found that the present compound has an excellent therapeutic effect of fibromyalgia compared to well-known compounds, and thus completed the present invention.

Thus, the present invention relates to:
[1] a prophylactic and/or therapeutic agent for fibromyalgia, containing (1S)-2-acetyl-1-(4-chloro-2-methoxyphenyl)-5-fluoro-1,2,3,9-tetrahydrospiro[β-carboline-4,1'-cyclopropane] represented by the formula:

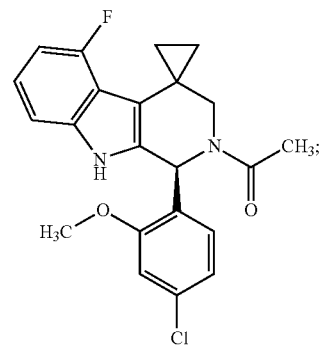 [SMILES: COc1cc(Cl)ccc1[C@H]1c2[nH]c3cccc(F)c3c2C2(CC2)CN1C(C)=O]

[2] a prophylactic and/or therapeutic agent for a fibromyalgia-associated disease, containing (1S)-2-acetyl-1-(4-chloro-2-methoxyphenyl)-5-fluoro-1,2,3,9-tetrahydrospiro[β-carboline-4,1'-cyclopropane] represented by the formula:

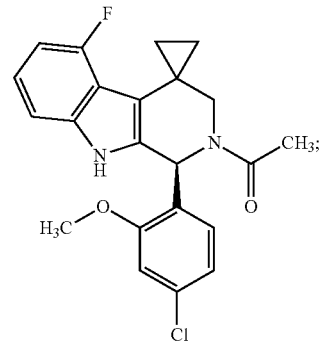 [SMILES: COc1cc(Cl)ccc1[C@H]1c2[nH]c3cccc(F)c3c2C2(CC2)CN1C(C)=O]

[3] an agent for amelioration of a fibromyalgia-associated symptom, containing (1S)-2-acetyl-1-(4-chloro-2-methoxyphenyl)-5-fluoro-1,2,3,9-tetrahydrospiro[β-carboline-4,1'-cyclopropane] represented by the formula:

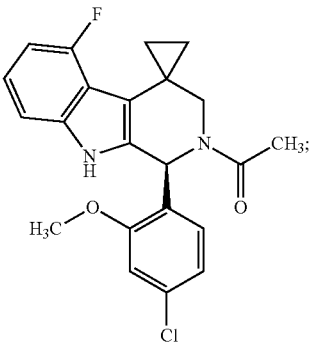 [SMILES: COc1cc(Cl)ccc1[C@H]1c2[nH]c3cccc(F)c3c2C2(CC2)CN1C(C)=O]

[4] the agent according to [2], wherein the fibromyalgia-associated disease is rheumatoid arthritis, Sjogren's syndrome, systemic lupus erythematosus, scleroderma, Behcet's disease, seronegative spondylitis, mixed connective tissue disease, interstitial cystitis or osteoarthritis;

[5] the agent according to [3], wherein the fibromyalgia-associated symptom is pain, fatigue, malaise, fever, Raynaud's phenomenon, night sweat, palpitation, respiratory discomfort, wheezing, dysphagia, interstitial cystitis-like symptom, menstruation disturbance, dysmenorrhea, weight fluctuation, heat and cold intolerance, temporomandibular joint disease, abdominal symptom, stool abnormality, hand swelling, stomatitis, cutaneous pruritis, skin rash, photosensitivity disorder, headache, headache dull, appendicular sensory disorder, finger tremor, dizziness, anacatesthesia, tinnitus, hearing loss, photophobia, visual impairment, muscular weakness, muscular sluggishness, carpal tunnel syndrome, restless legs syndrome, depressed mood, anxiety, restlessness, poor concentration, poor attention, amnesia or consciousness disorder;

[6] a medicament including, in combination, (1S)-2-acetyl-1-(4-chloro-2-methoxyphenyl)-5-fluoro-1,2,3,9-tetrahydrospiro[β-carboline-4,1'-cyclopropane] represented by the formula:

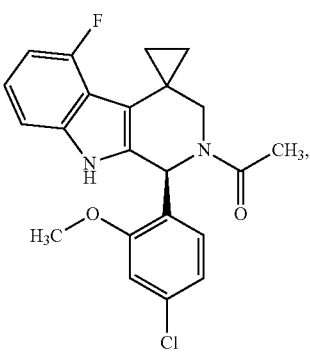 [SMILES: COc1cc(Cl)ccc1[C@H]1c2[nH]c3cccc(F)c3c2C2(CC2)CN1C(C)=O]

and at least one drug selected from the group consisting of pregabalin, duloxetine hydrochloride, milnacipran hydrochloride, tramadol, gabapentin, clonazepam, acetaminophen, aspirin, indomethacin, etodolac, celecoxib, loxoprofen, and diclofenac;

[7] a method for prophylaxis and/or therapy of fibromyalgia, including administering, to a mammal in the need of prophylaxis and/or therapy of fibromyalgia, an effective dose of (1S)-2-acetyl-1-(4-chloro-2-methoxyphenyl)-5-fluoro-1,2,3,9-tetrahydrospiro[β-carboline-4,1'-cyclopropane] represented by the formula:

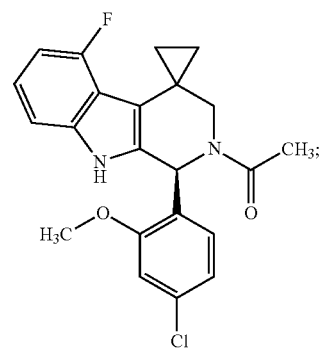 [SMILES: COc1cc(Cl)ccc1[C@H]1c2[nH]c3cccc(F)c3c2C2(CC2)CN1C(C)=O]

[8] use of (1S)-2-acetyl-1-(4-chloro-2-methoxyphenyl)-5-fluoro-1,2,3,9-tetrahydrospiro[β-carboline-4,1'-cyclopropane] represented by the formula:

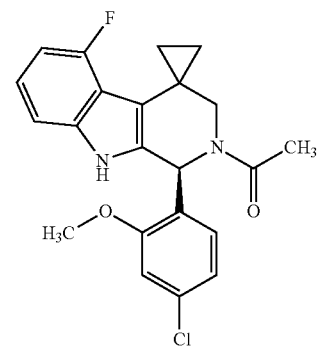 [SMILES: COc1cc(Cl)ccc1[C@H]1c2[nH]c3cccc(F)c3c2C2(CC2)CN1C(C)=O]

for manufacturing a prophylactic and/or therapeutic agent for fibromyalgia;

[9] (1S)-2-acetyl-1-(4-chloro-2-methoxyphenyl)-5-fluoro-1,2,3,9-tetrahydrospiro[β-carboline-4,1'-cyclopropane] represented by the formula:

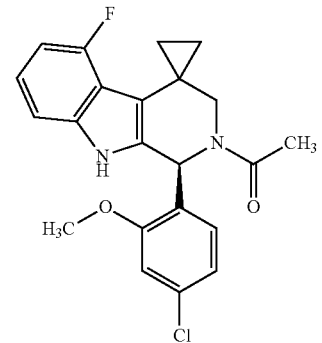 [SMILES: COc1cc(Cl)ccc1[C@H]1c2[nH]c3cccc(F)c3c2C2(CC2)CN1C(C)=O]

for use in prophylaxis and/or therapy of fibromyalgia; and

[10] a prophylactic and/or therapeutic agent for fibromyalgia containing a TSPO ligand.

Advantageous Effects of Invention

The present compound has an excellent therapeutic effect of fibromyalgia compared to well-known TSPO antagonists, and thus is useful as a medicament.

BRIEF DESCRIPTION OF DRAWINGS

FIG. 1 shows the pain threshold in a rat somatic hyperalgesia model on the non-challenged side (right hind paw) prior to administration on day 7 of administration of the present compound.

FIG. 2 shows the pain threshold in a rat somatic hyperalgesia model on the non-challenged side (right hind paw) 2 hours after administration on day 7 of administration of the present compound.

FIG. 3 shows the pain threshold in a rat somatic hyperalgesia model on the non-challenged side (right hind paw) prior to administration on day 7 of administration of the comparative compound.

FIG. 4 shows the pain threshold in a rat somatic hyperalgesia model on the non-challenged side (right hind paw) 2 hours after administration on day 7 of administration of the comparative compound.

DESCRIPTION OF EMBODIMENTS

The present invention is hereinafter specifically described.

In the present invention, the present compound, namely (1S)-2-acetyl-1-(4-chloro-2-methoxyphenyl)-5-fluoro-1,2,3,9-tetrahydrospiro[β-carboline-4,1'-cyclopropane] is represented by the following structural formula.

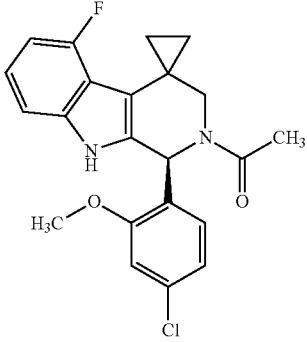 [SMILES: COc1cc(Cl)ccc1[C@H]1c2[nH]c3cccc(F)c3c2C2(CC2)CN1C(C)=O]

In the present invention, the present compound may be produced according to the method described in Example 36(2)→Example 38 in PTL 1.

As used herein, TSPO means translocator protein 18 kDa and means a receptor protein also referred to as MBR (mitochondrial benzodiazepine receptor) or PBR (peripheral benzodiazepine receptor).

As used herein, fibromyalgia means a disease which is diagnosed as fibromyalgia according to any one of or a combination of the American College of Rheumatology (ACR) Criteria for the Classification of Fibromyalgia (1990), the ACR Preliminary Diagnostic Criteria for Fibromyalgia (2010) or the Modification of the ACR Preliminary Diagnostic Criteria for Fibromyalgia (2011) as cited in the "Practice Guidelines for Fibromyalgia 2013", Chapter 3 "Diagnostic Criteria", Ed. Japan College of Fibromyalgia Investigation.

In the present invention, examples of the fibromyalgia-associated disease (associated disease) include rheumatoid arthritis, Sjogren's syndrome, systemic lupus erythematosus, scleroderma, Behcet's disease, seronegative spondylitis, mixed connective tissue disease, interstitial cystitis, osteoarthritis, chronic inflammatory demyelinating polyneuropathy (CIDP), cerebrospinal fluid hypovolemia, asthma, chronic obstructive pulmonary disease, chest-myalgia syndrome, hyperventilation syndrome, pharyngeal spasm, nervous cough, essential hypertension, angina, myocardial infarction, essential hypotension, orthostatic hypotension, arrhythmia, Raynaud's disease, neurocirculatory asthenia, gastroduodenal ulcer, gastroesophageal reflux disease (GERD), acute gastric mucosal lesion (AGML), chronic gastritis, ulcerative colitis, chronic hepatitis, chronic pancreatitis, biliary dyskinesia, neurological abdominal bloating, diffuse esophageal spasm, esophageal achalasia, merycism, aerophagy, gas retention syndrome, psychogenic vomiting, anorexia nervosa, hyperthyroidism, hypothyroidism, diabetes, bulimia, Pseudo-Bartter syndrome, deprivation dwarfism, renal glucosuria, psychogenic polydipsia, strabismus, parkinsonian syndrome, multiple sclerosis, tension headache, migraine, writer's cramp, visual fatigue, photophobia, dry eye, eye twitching, ptosis, ageusia, dysautonomia, tremor, tic, choreiform movement, dystonia, paresthesia, motor paralysis, astasia/abasia, aphonia, Basedow's disease, atopic dermatitis, breath-holding spell, repetitive abdominal pain, cyclic vomiting syndrome, encopresis, orthostatic dysregulation, nocturnal enuresis, stuttering, night terror, alopecia areata, alopecia universalis, contact dermatitis, hyperhidrosis, sunburn, eczema, trichotillomania, dysmorphophobia, intestinal adhesion, dumping syndrome, polysurgery, neurological abdominal bloating, post-plastic neurosis, disc herniation, cervico-omo-brachial syndrome, gout, spinal canal stenosis, lumbago, stiff neck, traumatic cervical syndrome, senile vaginitis, genital ulcer, vulvodynia, menopausal symptom, chronic pelvic pain syndrome, dysfunctional uterine bleeding, menstrual pain, premenstrual syndrome, menstrual abnormality, infertility, vulvar pruritus, coital pain, allergic rhinitis, sudden hearing loss, chronic sinusitis, stomatitis, Meniere's disease, patulous auditory tube, tubal obstruction, motion sickness, smell disorder, psychogenic hearing loss, pharyngeal paresthesia, hoarseness, psychogenic aphonia, temporomandibular joint disease, gingivitis, periodontal disease, alveolar osteitis, lockjaw, xerostomia, parageusia, trigeminal neuralgia, glossopharyngeal neuralgia, idiopathic glossodynia, denture maladjustment, postprosthetic neurosis, oropharyngeal hypersensitivity, chronic fatigue syndrome, perineal pain, chest pain and low back pain.

In the present invention, examples of the fibromyalgia-associated symptom (associated symptom) includes pain, fatigue, malaise, fever, Raynaud's phenomenon, night sweat, palpitation, respiratory discomfort, wheezing, dysphagia, interstitial cystitis-like symptom, menstruation disturbance, dysmenorrhea, weight fluctuation, heat and cold intolerance, temporomandibular joint disease, abdominal symptom, heartburn, stool abnormality, gastrospasm-like abdominal pain, upper abdominal pain, nausea, vomiting, anorexia, hand swelling, stomatitis, oral dryness, taste disorder, dry eye, cutaneous pruritus, skin rash, urticaria, photosensitivity disorder, chest pain, headache, headache dull, appendicular sensory disorder, finger tremor, dizziness, anacatesthesia, numbness, tinnitus, hearing loss, photophobia, visual impairment, muscular weakness, muscular sluggishness, carpal tunnel syndrome, restless legs syndrome, sleep disorder, sleep apnoea syndrome, depressed mood, insomnia, anxiety, restlessness, poor concentration, poor attention, amnesia, consciousness disorder, syncope, spasm, purpura, hair loss, frequent urination, miction pain and bladder spasm.

In the present invention, the TSPO ligand may include AC-5216, PBR28, DPA713, DAA1106, PK11195, compounds disclosed in Examples of PTL 1 and the like.

In the present invention, AC-5216 means N-benzyl-N-ethyl-2-(7-methyl-8-oxo-2-phenyl-7,8-dihydro-9H-purin-9-yl)acetamide (CAS registry No.: 226954-04-7), PBR28 means N-(2-methoxybenzyl)-N-[4-(phenoxy)pyridin-3-yl]acetamide (CAS registry No.: 253307-65-2), DPA713 means N,N-diethyl-2-[2-(4-methoxyphenyl)-5,7-dimethyl-pyrazolo[1,5-a]pyrimidin-3-yl]acetamide (CAS registry No.: 386297-97-8), DAA1106 means N-(2-phenoxy-5-fluorophenyl)-N-(2,5-dimethoxybenzyl)acetamide (CAS registry No.: 220551-92-8) and PK11195 means 1-(2-chlorophenyl)-N-methyl-N-(1-methylpropyl)isoquinoline-3-carboxamide (CAS registry No.: 85532-75-8).

[Toxicity]

The present compound has sufficiently low toxicity and thus can be safely used as a medicament.

[Medicinal Application]

The present compound has an antagonistic effect of TSPO, and thus is useful as a prophylactic and/or therapeutic agent for fibromyalgia and/or a fibromyalgia-associated disease. The present compound is further useful as an agent for amelioration of a fibromyalgia-associated symptom.

The present compound may be administered as a concomitant drug with another agent for 1) a complementation and/or enhancement of the above effect of the present compound, 2) an improvement of the kinetics/absorption the present compound or a reduction of the dosage of the present compound and/or 3) an alleviation of a side effect of the present compound.

A concomitant drug of the present compound with another agent may be administered in a form of a combination agent containing both components in one formulation or may be in a form to be administered as separate formulations. When separate formulations are administered, simultaneous administration and administration at different times are envisaged. When administered at different times, the present compound may be administered followed by another agent or another agent may be administered followed by the present compound, and the manners of administration thereof may be the same or different.

In the present invention, examples of benzodiazepine anti-anxiety agents include alprazolam, oxazepam, oxazolam, cloxazolam, clorazepate dipotassium, chlordiazepoxide, diazepam, tofisopam, triazolam, prazepam, fludiazepam, flutazolam, flutoprazepam, bromazepam, mexazolam, medazepam, ethyl loflazepate and lorazepam.

In the present invention, examples of thienodiazepine anti-anxiety agents include etizolam and clotiazepam.

In the present invention, examples of non-benzodiazepine anti-anxiety agents include tandospirone citrate, hydroxyzine hydrochloride, zopiclone and zolpidem tartrate.

In the present invention, examples of neurokinin-1 antagonists include aprepitant and fosaprepitant meglumine.

In the present invention, examples of tricyclic antidepressants include amitriptyline hydrochloride, imipramine hydrochloride, clomipramine hydrochloride, dosulepin hydrochloride, nortriptyline hydrochloride, lofepramine hydrochloride, trimipramine maleate and amoxapine.

In the present invention, examples of tetracyclic antidepressants include maprotiline hydrochloride, mianserin hydrochloride and setiptiline maleate.

In the present invention, examples of monoamine oxidase (MAO) inhibitors include safrazine hydrochloride.

In the present invention, examples of serotonin and noradrenaline reuptake inhibitors (SNRIs) include milnacipran hydrochloride, venlafaxine hydrochloride and duloxetine hydrochloride.

In the present invention, examples of selective serotonin reuptake inhibitors (SSRIs) include fluvoxamine maleate, paroxetine hydrochloride, fluoxetine hydrochloride, citalopram hydrochloride and sertraline hydrochloride.

In the present invention, examples of serotonin reuptake inhibitors include trazodone hydrochloride.

In the present invention, examples of noradrenergic and selective serotonergic antidepressants include mirtazapine.

In the present invention, examples of noradrenaline and dopamine disinhibitors include agomelatine.

In the present invention, examples of serotonin reuptake accelerating agents include tianeptine.

In the present invention, examples of N-methyl-D-aspartate receptor inhibitors include memantine.

In the present invention, examples of dopamine precursors include levodopa.

In the present invention, examples of dopamine receptor agonists include bromocriptine, pramipexole and ropinirole.

In the present invention, examples of dopamine receptor antagonists include levomepromazine and sulpiride.

In the present invention, examples of COMT inhibitors include entacapone and opicapone.

In the present invention, examples of cholinesterase inhibitors include donepezil and rivastigmine.

In the present invention, examples of anticholinergic agents include trihexyphenidyl, biperiden, ipratropium bromide and mepenzolate bromide.

In the present invention, examples of serotonin-dopamine antagonists include risperidone, perospirone hydrochloride hydrate, quetiapine fumarate and olanzapine.

In the present invention, examples of voltage-dependent $Ca^{2+}$ channel binding agents include pregabalin, gabapentin and gabapentin enacarbil.

In the present invention, examples of opioid receptor agonists include tramadol, buprenorphine and pentazocine.

In the present invention, examples of antiepileptic agents include phenobarbital, phenytoin, carbamazepine, valproic acid, clonazepam, levetiracetam, topiramate and lamotrigine.

In the present invention, examples of antivertiginous agents include difenidol and betahistine.

In the present invention, examples of prokinetic agents include trimebutine maleate and calcium polycarbophil.

In the present invention, examples of histamine $H_2$ receptor antagonists include cimetidine, ranitidine, famotidine, nizatidine and lafutidine.

In the present invention, examples of proton pump inhibitors include omeprazole, lansoprazole and rabeprazole.

In the present invention, examples of muscarine receptor antagonists include pirenzepine.

In the present invention, examples of muscarine receptor stimulating agents include pilocarpine hydrochloride.

In the present invention, examples of defensive factor enhancers include gefarnate, teprenone, sucralfate, aldioxa, cetraxate hydrochloride and ornoprostil.

In the present invention, examples of prostaglandin derivatives include ornoprostil and misoprostol.

In the present invention, examples of opioid agonists include asimadoline and nalfurafine.

In the present invention, examples of 5-$HT_4$ agonists include tegaserod, cisapride and mosapride citrate.

In the present invention, examples of 5-$HT_3$ antagonists include ramosetron, alosetron and cilansetron.

In the present invention, examples of chloride channel activators include lubiprostone.

In the present invention, examples of guanylate cyclase agonists include linaclotide.

In the present invention, examples of bulk laxatives include methylcellulose, carmellose and lactulose.

In the present invention, examples of saline cathartics include magnesium sulphate and magnesium oxide.

In the present invention, examples of irritant cathartics include picosulfate, lactulose, castor oil, *senna* and rhubarb.

In the present invention, examples of affinity polyacrylic resins include calcium polycarbophil.

In the present invention, examples of nonsteroidal anti-inflammatory drugs include acetaminophen, aspirin, indomethacin, etodolac, celecoxib, loxoprofen, ketoprofen and diclofenac.

In the present invention, examples of steroids include dexamethasone, betamethasone and prednisolone.

In the present invention, examples of anti-cholinesterase inhibitors include pyridostigmine bromide.

Examples of another agent that may be used with the present compound in combination include serotonin and noradrenaline reuptake inhibitors (SNRIs), selective serotonin reuptake inhibitors (SSRIs), serotonin reuptake inhibitors, noradrennergic and specific serotonergic antidepressants (NaSSAs), noradrenaline and dopamine disinhibitors (NDDIs), selective serotonin reuptake accelerating agents (SSREs), serotonin-dopamine antagonists, voltage-dependent $Ca^{2+}$ channel binding agents, opioid μ receptor agonists, muscarine receptor antagonists, muscarine receptor stimulating agents, benzodiazepine anti-anxiety agents, thienodiazepine anti-anxiety agents, non-benzodiazepine anti-anxiety agents, tricyclic antidepressants, tetracyclic antidepressants, monoamine oxidase (MAO) inhibitors, triazolopyridine antidepressants, N-methyl-D-aspartate (NMDA) receptor inhibitors, nonsteroidal antiinflammatory drugs (NSAIDs), steroids, CRF antagonists, neurokinin-1 (NK1) antagonists, glycine transporter inhibitors, dopamine precursors, dopamine receptor agonists, dopamine receptor antagonists, catechol-O-methyltransferase (COMT) inhibitors, cholinesterase inhibitors, neurotensin antagonists, anti-cholinergic agents, central stimulants, antiepileptic agents, antivertiginous agents, prokinetic agents, histamine $H_2$ receptor antagonists, proton pump inhibitors, defensive factor enhancers, prostaglandin derivatives, opioid agonists, $5-HT_4$ agonists, $5-HT_3$ antagonists, chloride channel activators, guanylate cyclase agonists, bulk laxatives, saline cathartics, irritant cathartics, affinity polyacrylic resins, anti-cholinesterase inhibitors, extracts of inflamed skin of domestic rabbits inoculated with vaccinia virus (neurotropin (trade name)) and salazosulfapyridine.

EXAMPLES

The present invention is hereinafter specifically described by way of Examples which do not limit the present invention.

EXPERIMENTAL EXAMPLES

Biological experimental examples are hereinafter described. According to the experimental methods, the effect of the present compound was validated.

Biological Example 1: Efficacy in a Rat Somatic Hyperalgesia Model

SD male rats (Charles River Laboratories Japan, Inc., 5 weeks old upon usage) were used. Under isoflurane anaesthesia, rats were intramuscularly administered with 100 μL of acidic saline of pH 4.0 in the left gastrocnemius. After 5 days of administration, rats again received 100 μL of acid saline in the left gastrocnemius. In the normal group, rats were intramuscularly administered with 100 μL of saline twice in total with 5 days apart in the left gastrocnemius (see Muscle Nerve, vol. 24, pp. 37-46, 2001).

The pain threshold was measured on a Randall-Selitto pressure analgesy-meter (Ugo Basile). Briefly, rats were securely fixed and uniformly and continuously increasing pressure was applied to the hind paws. The pressure at which rats showed the escape response was recorded as a pain threshold (g). For each of the left and right hind paws, tests were carried out three times at each evaluation point and the values were averaged to obtain the pain threshold.

On the day before the first administration of acid saline, the pain threshold was measured and rats which showed the pain threshold of 140 g or more for both left and right hind paws were selected. At day 6 or 7 of the second administration of acid saline, the pain threshold was measured and rats which showed the pain threshold of 135 g or less for both left and right hind paws were selected. On the next day, the pain threshold was measured again and rats which showed the pain threshold of 130 g or less for both left and right hind paws were selected and divided into groups. For the normal group, rats were arbitrarily selected from those showing the pain threshold on the day before the first administration of acid saline of 140 g or more for both left and right hind paws. After being divided into groups, administration of the test compound (the present compound (the compound described in Example 38 of PTL 1), comparative compound A (the compound described in Example 38(5) of PTL 1), comparative compound B (the compound described in Example 41(2) of PTL 1), comparative compound C (1-(2-chlorophenyl)-N-methyl-N-(1-methylpropyl) isoquinoline-3-carboxamide (PK11195), CAS registry No.: 85532-75-8), a control substance (duloxetine hydrochloride, pregabalin) or a vehicle (0.5 w/v % methylcellulose 400 cP solution)) was started on the same day. On day 1 and day 7 of administration of each drug solution, the pain threshold on left and right hind paws was measured in a blind manner 2 hours after the first administration. Duloxetine hydrochloride was orally administered once a day and other agents were orally administered twice a day.

As a result, as shown in FIG. 1 and FIG. 2 (in each figure, ### means $p<0.001$ over the normal group in Welch's test; $$ means $p<0.01$ over the control group in Welch's test; $$$ means $p<0.001$ over the control group in Welch's test; * means $p<0.05$ over the control group in Dunnett's test; and *** means $p<0.001$ over the control group in Dunnett's test), the pain thresholds on day 7 of administration of each drug solution on the right hind paw (non-challenged side) before administration and 2 hours after administration decreased in the control group compared to the normal group. The present compound at a dose of 0.1, 1 or 10 mg/kg suppressed this decrease of the pain threshold to a similar extent as duloxetine hydrochloride (30 mg/kg) and pregabalin (20 mg/kg). Meanwhile, as shown in FIG. 3 and FIG. 4 (in each figure, ### means $p<0.001$ over the normal group in t-test; * means $p<0.01$ over the control group in t-test; and *** means $p<0.001$ over the control group in t-test), all comparative compound A and comparative compound B, which are structural analogues of the present compound, and comparative compound C, which is a well-known TSPO antagonist, at a dose of 1 mg/kg did not show the efficacy for the pain threshold which was decreased in the control group compared to the normal group. The tendency of the results observed on right hind paws (non-challenged side) as described above were also observed on left hind paws (challenged side).

From these results, it was revealed that only the present compound among TSPO antagonists shows significant suppression of the decrease of the pain threshold caused by acid saline.

INDUSTRIAL APPLICABILITY

The present compound can particularly suppress a decrease of the pain threshold among TSPO antagonists, and thus is useful as a medicament for use in prophylaxis and/or therapy of fibromyalgia.

The invention claimed is:

1. A method for prophylaxis and/or treatment of fibromyalgia, comprising administering, to a mammal in need of thereof an effective amount of (1S)-2-acetyl-1-(4-chloro-2-methoxyphenyl)-5-fluoro-1,2,3,9-tetrahydrospiro[β-carboline-4,1'-cyclopropane] of the following chemical formula:

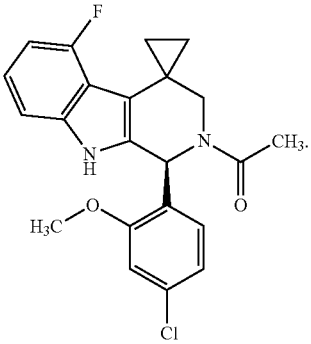 [SMILES: COc1cc(Cl)ccc1[C@H]1c2[nH]c3cccc(F)c3c2C2(CC2)CN1C(C)=O]

2. A method for suppressing a decrease in threshold of pain in a subject, comprising administering, to the subject an effective amount of (1S)-2-acetyl-1-(4-chloro-2-methoxyphenyl)-5-fluoro-1,2,3,9-tetrahydrospiro[β-carboline-4,1'-cyclopropane] of the following chemical formula:

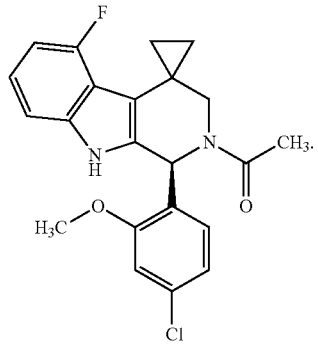 [SMILES: COc1cc(Cl)ccc1[C@H]1c2[nH]c3cccc(F)c3c2C2(CC2)CN1C(C)=O]

3. The method according to claim 1, wherein the effective amount is 0.1-10 mg/kg daily.

* * * * *